(12) United States Patent
Collerais

(10) Patent No.: US 11,154,310 B2
(45) Date of Patent: Oct. 26, 2021

(54) CRANIAL PERFORATOR

(71) Applicant: VITALYS SURGICAL, Vitré (FR)

(72) Inventor: Pierre-Yves Collerais, Vitré (FR)

(73) Assignee: Vitalys Surgical, Vitré (FR)

( * ) Notice: Subject to any disclaimer, the term of this patent is extended or adjusted under 35 U.S.C. 154(b) by 0 days.

(21) Appl. No.: 16/189,107

(22) Filed: Nov. 13, 2018

(65) Prior Publication Data
US 2019/0142439 A1 May 16, 2019

(30) Foreign Application Priority Data

Nov. 13, 2017 (FR) ...................... 1760655

(51) Int. Cl.
*A61B 17/16* (2006.01)
*A61B 90/00* (2016.01)

(52) U.S. Cl.
CPC ...... *A61B 17/1695* (2013.01); *A61B 17/1617* (2013.01); *A61B 90/03* (2016.02); *A61B 17/162* (2013.01); *A61B 17/1628* (2013.01); *A61B 2090/034* (2016.02); *A61B 2090/08021* (2016.02)

(58) Field of Classification Search
CPC ............ A61B 17/1695; A61B 17/1615; A61B 17/1617; A61B 17/162; A61B 17/1633; A61B 2090/035; A61B 2090/031; A61B 2090/034
See application file for complete search history.

(56) References Cited

U.S. PATENT DOCUMENTS

| 5,330,480 A | 7/1994 | Meloul et al. |
| 2009/0024129 A1* | 1/2009 | Gordon .............. A61B 17/1617 606/80 |
| 2017/0027594 A1* | 2/2017 | Ujvari ................ A61B 17/1617 |

FOREIGN PATENT DOCUMENTS

| WO | 2009012457 A1 | 1/2009 |
| WO | WO-2009021933 A1 * | 2/2009 ......... A61B 17/1695 |
| WO | 2015150844 A1 | 10/2015 |

OTHER PUBLICATIONS

Written Opinion on the Patentability of the Invention; National Registration No. FR1760655; Filing Date: Nov. 13, 2017.

* cited by examiner

*Primary Examiner* — Kevin T Truong
*Assistant Examiner* — Lisa Nguyen
(74) *Attorney, Agent, or Firm* — Thomas|Horstemeyer LLP

(57) ABSTRACT

Cranial perforator (1) comprising a rotating element (10) capable of being fixed to a driving element, a first drill-head (20) and a second drill-head (30), clutch means (50) disposed on the first drill-head (20) and the rotating element (10) means of disengagement (60) from a engaged position of the first drill-head (20) to an idle position of the first drill-head (20) and a casing (40) fixed at one of its extremities to the rotating element (10) and partly encasing the second drill-head (30).

10 Claims, 6 Drawing Sheets

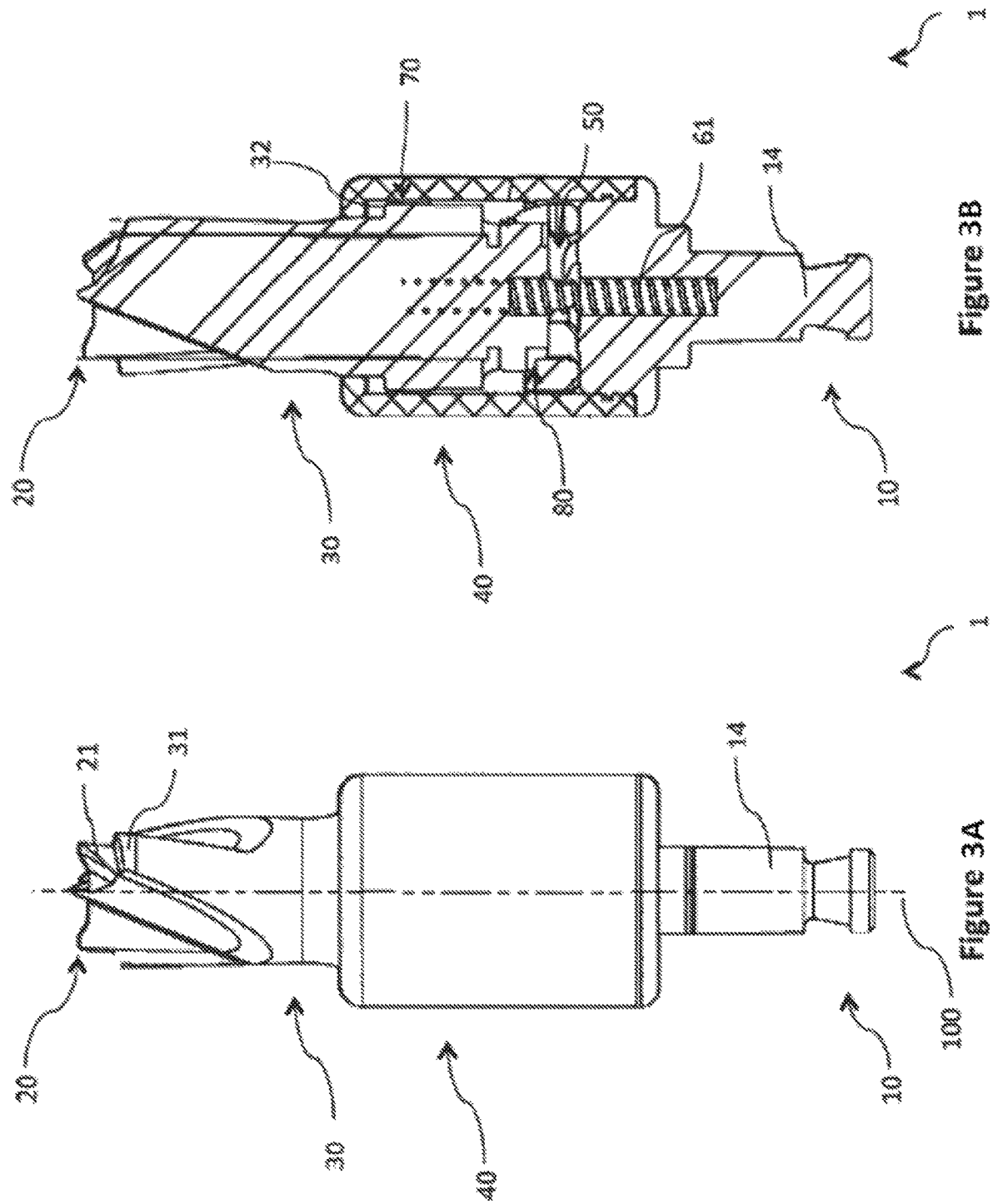

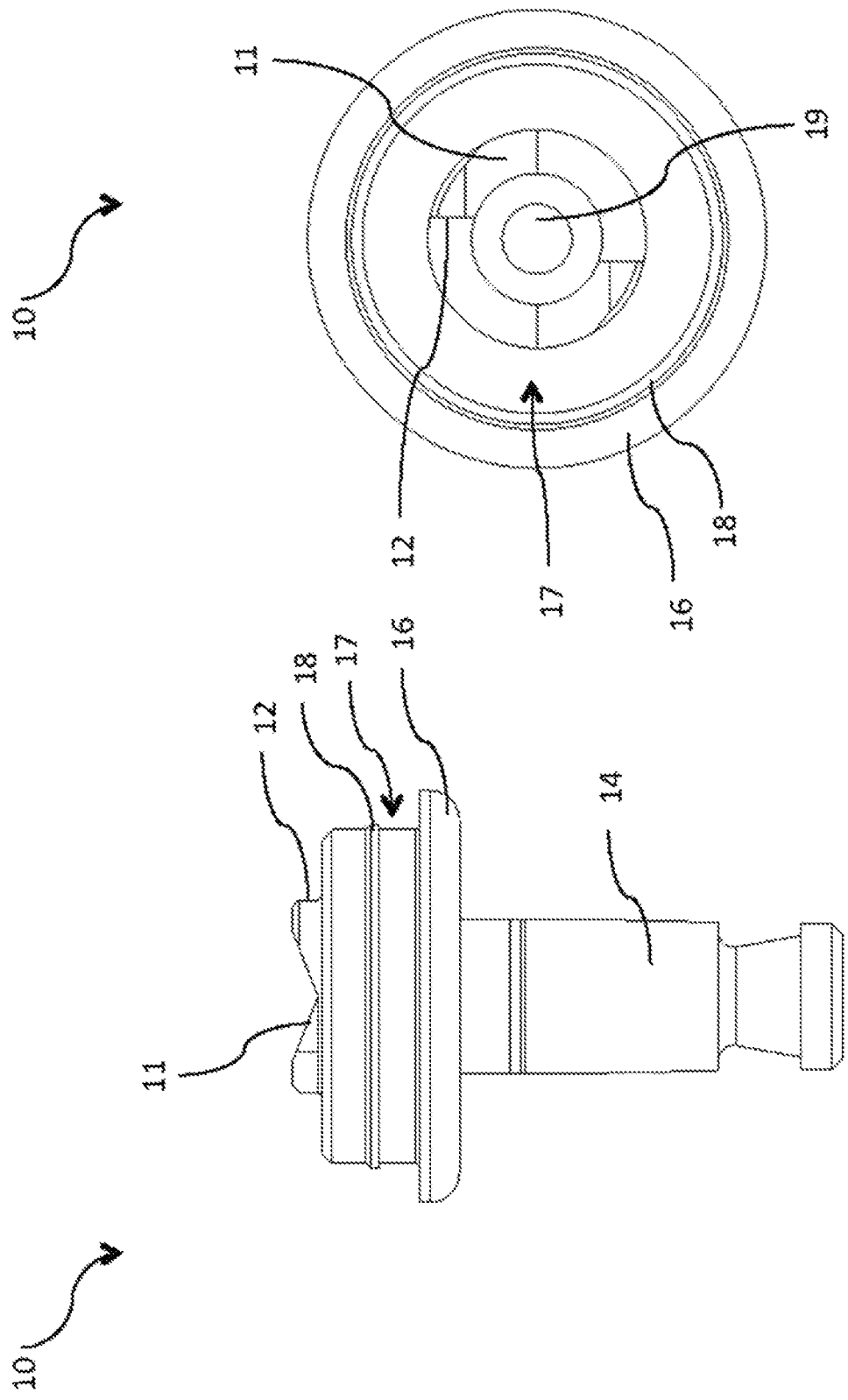

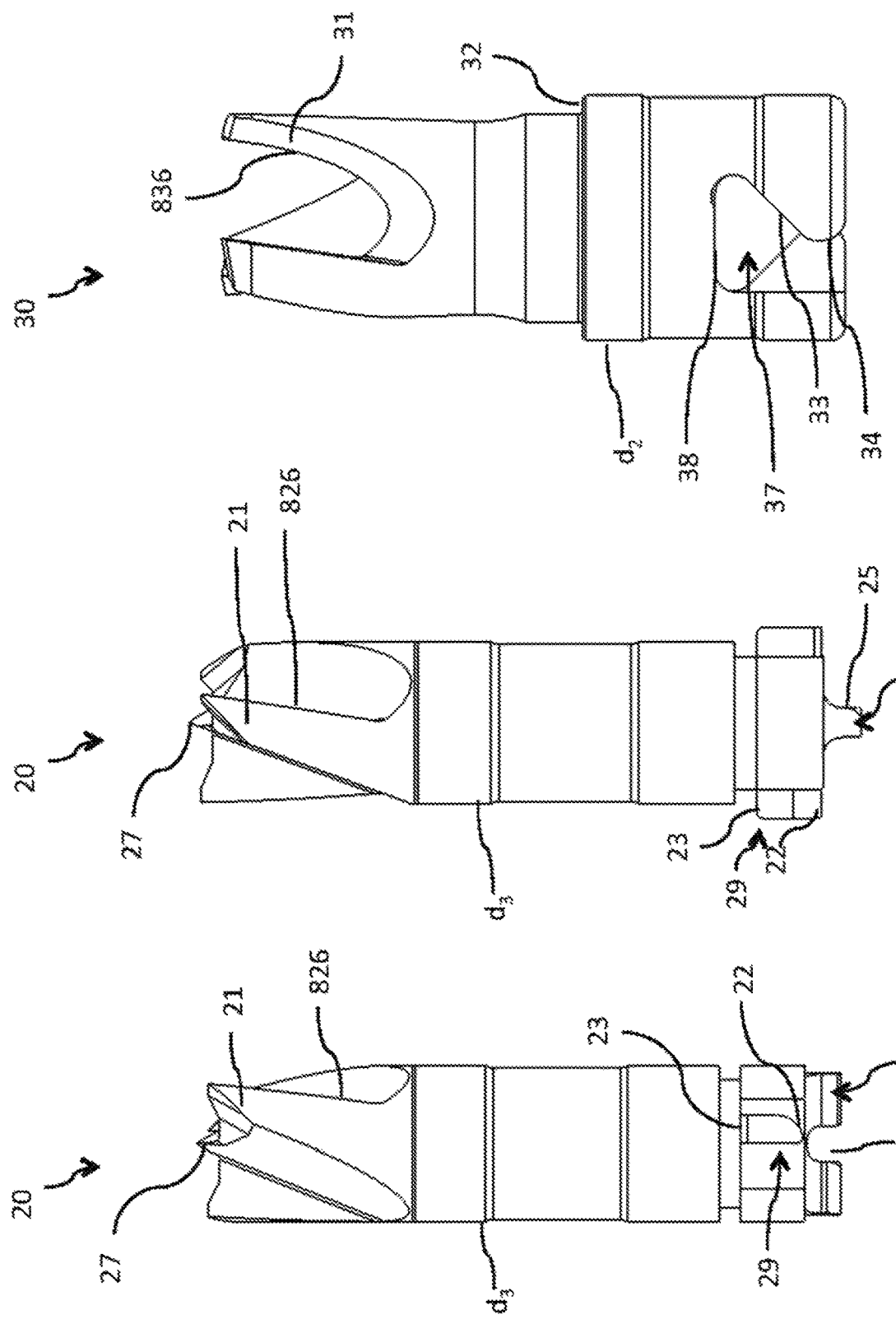

CRANIAL PERFORATOR

CROSS-REFERENCE TO RELATED APPLICATIONS

This application claims the priority to and benefit of French Patent Application No. 1760655, filed Nov. 13, 2017, which is herein incorporated by reference in its entirety.

FIELD OF INVENTION

The field of the invention is that of surgical instruments.

More specifically, the invention relates to surgical tools that are conventionally used by neurosurgeons in order to make skull perforations for patients suffering from certain pathologies. These perforations are made after the tissues covering the zone of the skull that has to be perforated have been preliminarily removed and after this zone has been scraped. Generally, a minimum of three trepanations or burr holes are drilled into the skull. These trepanations are followed operations of sawing between the burr holes so as to remove a cranial segment and thus open up an access for surgery.

Such tools are usually called cranial perforators or trepans and are intended to be connected to the end of a surgical instrument or of a surgical motor capable of driving this tools in a rotational motion.

BACKGROUND

Prior-art cranial perforators generally comprise two drill-heads. A first drill-head or "small" drill-head is housed within a second drill-head or "large" drill-head, in such a way that the cutting zone of the first drill-head slightly surpasses the cutting zone of the second drill-head. A general principle of the use of these drill-heads for the perforation of a skull is the application, first of all, of the first drill-head against the surface of the skull that has to be perforated by exerting a certain degree of pressure, which engages the first drill-head with the surgical motor with which the cranial perforator is linked. Then, the surgical motor is put into operation, thus rotationally driving the first drill-head and the second drill-head, the second drill-head being fixedly attached to the first drill-head. When the first drill-head has nearly passed through the bone mass of the skull, the resistance to its progress diminishes, and this disengages the first drill-head from the surgical motor. Although the surgical motor continues to rotate, the first drillhead and the second drill-head both stop rotating. This makes it possible especially to avoid damaging the dura mater that adheres to the bone inside the cranial cavity.

Prior-art cranial perforators are conventionally constituted by a large number of mutually assembled parts. The fact that there are many of these parts makes prior-art cranial perforators complicated to manufacture/machine and assemble.

In addition, the fact that there a large number of these parts means that there is an accumulation of uncertainty over the sizing of each of these many parts and an accumulation of uncertainty over the positioning of each part relative to other parts.

Finally, the disengagement of the first drill-head from the surgical motor is fairly slow relative to the drilling speed, and this can lead, in certain circumstances, to varying degrees of damage to the dura mater.

The general structure of one of these perforators has especially been described in a French patent application published under number FR 2919991. Such a structure is shown schematically in FIG. 1.

The cranial perforator 200 shown in FIG. 1 comprises a rotating element 201 forming a casing, one end of which can be connected to a surgical motor (not shown) implemented in order to put the rotating element 201 into rotation. The rotating element 201 has a first bore hole 220, a portion 225 of which is tapped.

An intermediate ring 301 is screwed into the tapped portion 225 of the rotating element 201. The intermediate ring 301 is traversed at its midpoint by a drill hole 311 that extends essentially along its longitudinal axis. This intermediate ring 301 is made out of bronze because bronze has high resistance to friction and has high lubricant capacity.

A transmission rod 401 is mounted so as to be slidingly mobile within the drill hole 311 so that it can be translated and pivoted thereon. A first extremity of the transmission rod 401 has a shoulder 411, the external diameter of which is greater than the diameter of the drill hole 311 in such a way that the transmission rod 401 cannot be translated within the interior of the drill hole 311 beyond a certain extent.

A first drill-head 510 is screwed to a threaded portion 422 of the second extremity of the transmission rod 401.

A compression bead 601 is interposed between the first drill-head 510 and the second extremity of the transmission rod 401.

A second drill-head 520, within which the first drill-head 510 is housed, is linked in rotation to the first drill-head 510. To this end, the first drill-head 510 and the second drill-head 520 respectively have elements of complementary shape (not shown) capable of getting engaged together in such a way that the rotation of the first drill-head 510 drives the rotation of the second drill-head 520.

A clutch means 350 between the first drill-head 510 and the intermediate ring 301 thus makes it possible, in an engaged position, for the first drill-head 510 to be linked in rotation with the intermediate ring 301 when the rotating element 201 is put into rotation and, in a resting or idle position, for the first drill-head 510 to be not linked in rotation with the intermediate ring 301, when the rotating element 510 is put into rotation.

A compression spring 701 is disposed between a housing 428 made for this purpose at the first extremity of the transmission rod 401 and a receptacle 228 made for this purpose at the end of the first bore hole 220 of the rotating element 201. It makes it possible to pass from the engaged position to the idle position when the axial force exerted on the first drill-head is not sufficient.

The rotating element 201 has a second bore hole 240 within which the second drill-head 520 gets housed. The second bore hole 240 has a shoulder 246 on which the second drill-head 520 is capable of coming to a stop.

A cranial perforator such as the one shown in FIG. 1 nevertheless has numerous disadvantages.

It has in all seven different parts: a first drill-head 510, a second drill-head 520, a compression bead 601, a transmission rod 401, an intermediate ring 301, a compression spring 701 and a rotating element 201. The result of this is manufacturing/machining complexity and complexity of assembling the parts together. This also results in a possible accumulation of sizing errors for each of the parts, giving rise to a deviation in the sequence of dimensions of the different parts of the cranial perforator relative to one another. Besides, apart from sizing errors, the deviation in the sequence of dimensions can also be accentuated by wrong assembly. Wrong assembly can especially result from incomplete screwing between the parts. Now, the cranial perforator of FIG. 1 has two mutual screwings of parts. The consequence of excessive deviation of the sequence of dimensions of the parts of the cranial perforator can be a lack of reliability of the cranial perforator for a drilling of the skull or even, if the deviation is excessive, dangerousness of the cranial perforator in the drilling of the skull.

The intermediate ring 301 made of bronze is especially of little advantage. As referred to here above, it is a source of possible positioning error in the cranial perforator during assembly, especially because of possible incomplete screwing within the rotating element 201. In addition, it has a substantial surface area of friction with the transmission rod 401. In addition, bronze is not a biocompatible material and it is preferable not to use it since micro-particles can be projected when the cranial perforator perforates a skull. Finally, since the cranial perforator of FIG. 1 can easily be dismantled by unscrewing and/or disengagement of the different parts, it can ultimately be re-utilized several times after sterilization in a steamer of all the parts that form it. Now, although they are sterilized in a steamer, the drill-heads of the cranial perforator can still transmit the Creutzfeldt-Jakob prion. It is therefore necessary to ensure the single-time use of each cranial perforator.

BRIEF SUMMARY OF INVENTION

The goal of the invention is to overcome at least some of the drawbacks of the prior art.

It is a goal of the invention to provide a cranial perforator that has an optimized structure that is reliable and sure during the drilling of a skull.

In particular, it is a goal of the invention to provide a cranial perforator that contains a limited number of parts.

It is another goal of the invention, in at least some advantageous embodiments, to provide a cranial perforator that comprises parts that are simple to manufacture/machine.

It is another goal, according to at least certain advantageous embodiments, to provide a cranial perforator that comprises parts that are easy to assemble with each other.

It is another goal, according to at least certain advantageous embodiments, to provide a cranial perforator the structure of which ensures single-time use.

It is another goal, according to at least certain advantageous embodiments, to provide a cranial perforator with improved disengagement.

The invention relates to a cranial perforator comprising: a rotating element, a first drill-head, a second drill-head, clutch means for engagement between the first drill-head and the rotating element; means of disengagement between the first drill-head and the rotating element and a casing.

The rotating element is capable of being fixed to a driving element.

The first drill-head and the second drill-head are capable of rotating about a same axis and of moving in translation along this axis. Each of them has, at one of their extremities, a plurality of teeth. The first drill-head is housed within the second drill-head. The first drill-head comprises at least one supporting surface capable of abutting the second drill-head when the first drill-head is put into rotation about its axis and, at least one second supporting surface capable of abutting the second drill-head when the first drill-head is driven by a motion of translation moving away from the rotating element along its axis.

The clutch means disposed on the first drill-head and the rotating element make it possible, in an engaged position, for the first drill-head to be linked in rotation with the rotating element when the rotating element is put into rotation and, in an idle position, for the first drill-head to be not linked in rotation with the rotating element when the rotating element is put into rotation.

The means of disengagement enable a disengagement from the engaged position towards the idle position.

The casing is fixed at one of its extremities to the rotating element and partly encases the second drill-head. The second drill-head is linked to the casing by a sliding pivot link and comprises a supporting surface capable of abutting the casing when the second drill-head is driven by a movement of translation moving away from the rotating element along its axis.

Thus, the cranial perforator according to the invention comprises neither the intermediate ring nor the transmission rod.

To ensure functions similar to those performed by these parts in the cranial perforator of the prior art, the cranial perforator according to the invention comprises especially a sliding pivot link linking the casing to the second drill-head. This sliding pivot link ensures perfect rotation of the second drill-head about its axis and also guides the second drill-head in translation along its axis. The first supporting surface of the first drill-head, capable of abutting the second drill-head when the first drill-head is put into rotation, enables the rotation of the first and second drill-head to be linked. The second supporting surface of the first drill-head, capable of abutting the second drill-head when the first drill-head is driven by a movement of translation moving away from the rotating element along its axis, and the supporting surface of the second drill-head, capable of abutting the casing when the second drill is driven by a movement of translation moving away from the rotating element along its axis, make it possible to limit, to a certain extent, the amplitude of translation of the first and second drill-heads along their axis.

The clutch means are moreover directly disposed between the rotating element and the first drill. No intermediate part is therefore disposed between the rotating element and the first drill to ensure their engagement.

The casing of the cranial perforator according to the invention ensures that the rotation of the second drill-head and of the first drill-head take place precisely about their axis of rotation. The casing also makes it possible to limit the amplitude of a motion of translation of the first and second drill-heads along their axis to a certain extent.

Preferably, the casing comprises a cylindrical section with a diameter greater than the diameter of a cylindrical section of the second drill-head. The sliding pivot link is advantageously formed by at least one lip protruding out of an external surface of the cylindrical section of the second drill-head or an internal surface of the cylindrical section of the casing. The utility of such a sliding pivot link is that it presents a low friction surface.

The sliding pivot link can especially be formed by two lips protruding out of an external surface of the cylindrical section of the second drill-head or out of an internal surface of the cylindrical section of the casing.

Preferably, the supporting surface of the second drill-head, capable of abutting the casing when the second drill-head is driven by a movement of translation moving away from the rotating element along its axis, is formed by a shoulder of the second drill-head, the shoulder of the second drill-head being capable of abutting a shoulder of the casing.

Advantageously, the casing is fixed to the rotating element by an irreversible elastic interlocking of the casing with the rotating element. The term "elastic interlocking" refers to a mode of assembly in which the elements are deformed during the insertion of one into the other. The term "irreversible" is understood to mean that when the casing and the rotating element are elastically interlocked with one another, disassembly cannot be obtained except by breaking the casing and/or the rotating element. The irreversible elastic interlocking of the casing with the rotating element makes it impossible to dismantle the cranial perforator. Thus, the cranial perforator cannot be cleaned, decontaminated and/or sterilized for second use. The irreversible elastic interlocking of the casing with the rotating element therefore ensures a single-time use of the cranial perforator of the invention. The irreversible elastic interlocking can especially be obtained by means of a groove-tongue system, the elements of which are respectively disposed on the rotating element and on the casing, with the tongue being inserted into the groove.

The rotating element is capable of being fixed to a driving element such as a surgical motor. The rotating element possesses especially, at one of its extremities, a tip adapted to being fixed to a driving element. The driving element, at the other of its extremities, has clutch means enabling engagement with the first drill-head.

The first drill-head and the second drill-head each have a plurality of teeth at one of their extremities. The first drill-head is housed within the second drill-head.

According to an advantageous characteristic, each of the teeth has a cutting face that extends along a plane that is essentially parallel to and offset relative to the axis of the first drill-head (and the second drill-head respectively). This particular geometry facilitates the formation of fine bone shavings during the perforation of the skull and improves the flow and removal of these shavings. These shavings could for example be re-utilized to fill in the vacant spaces left between the cranial segment and the skull when this skull is closed and to recolonize the bone of the skull and obtain a joining, at least in the middle term, of the cranial segment with the skull.

According to another advantageous characteristic of the invention, each of the teeth has cutting zones, the cutting zones forming protrusions and extending essentially from the periphery of the extremity having a plurality of teeth of the first drill-head (and the second drill-head, respectively) towards a hollowed-out central zone. This particular geometry makes it possible to approach the surface of the skull to be drilled from the periphery of the first drill-head (and the second drill-head respectively) so that, at the end of the drilling, there is a persisting portion of circular, uncut bone, also called a patch of bone, corresponding to the hollowed central zone. The persistence of such a patch of bone, at the end of drilling operation, protects the dura mater covering the internal surface of the skull and thus prevents it from being damaged.

Preferably, the first drill-head has a centering tip. The implementing of such a centering tip makes it easier to initiate the drilling operation and especially prevents the trepan from slipping. This improves the drilling precision, security and comfort of use.

The first drill-head has a first supporting surface capable of abutting the second drill-head when the first drill-head is put into rotation about the axis. This enables the second drill-head to be put into rotation when the first drill-head is put into rotation. Such an abutment can be formed by a spur-notch system, the elements of which are disposed respectively on the first drill-head and on the second drill-head, the spur passing through the notch and being capable of abutting against it.

The first drill-head comprises a second supporting surface capable of abutting the second drill-head when the first drill-head is driven by a movement of translation moving away from the rotating element along its axis. This limits the amplitude of a movement of translation of the first drill-head relative to the second drill-head. Such an abutment can be formed by a shoulder of the first drill-head capable of abutting a shoulder of the second drill-head.

The clutch means are disposed on the first drill-head and the rotating element. They make it possible, in an engaged position, for the first drill-head to be linked in rotation with the rotating element when the rotating element is put into rotation and, in an idle position, for the first drill-head to be not linked in rotation with the rotating element when the rotating element is put into rotation.

Preferably, the clutch means between the first drill-head and the rotating element comprise at least one inclined plane and a blocking surface disposed on an inclined plane of said drill-head or on an inclined plane of said rotating element and at least one finger having a supporting surface capable of coming into contact with a blocking surface in the engaged position, said at least one finger being disposed on the other one of said first drill-head or said rotating element. These clutch means enable gradual engagement of the first drill-head with the rotating element. In other words, the passage of the first drill-head into the engaged position can take place gently and without any jerks.

The means of disengagement make it possible to maintain the first drill-head in an idle position when the axial force exerted on the first drill-head is not sufficient.

According to a preferred characteristic of the invention, the disengagement means comprise a return means, such as a compression spring, that tends to bring the first drill-head back into the idle position. The return means are disposed between the first drill-head and the rotating element.

Advantageously, the means of disengagement furthermore comprise said at least first supporting surface of said first drill-head and at least one ramp disposed on said second drill-head and inclined relative to its axis, said at least first supporting surface of said first drill-head, capable of abutting said second drill-head, being capable of forming a sliding link when said first drill-head is put into rotation. The transmission of the torque between the first drill-head and the second drill-head at the level of a sliding link inclined relative to the axis of the drill-heads thus enables the creation of an axial component or force facilitating the disengagement of the first drill-head, i.e. its rapid return to the idle position.

Advantageously, the angle formed between said at least one ramp and said axis ranges from 15° to 75° relative to said axis, preferably from 30° to 60° relative to said axis, and is more preferably equal to 45° relative to said axis.

According to one particular embodiment, the first drill-head comprises two first supporting surfaces capable of forming two sliding links with two ramps disposed on the second drill-head. The two ramps and the two supporting surfaces respectively do not get superimposed by rotation by an angle of 180° along said axis. This ensures a unique position of the teeth of the first drill-head relative to the teeth of the second drill-head.

According to one preferred characteristic of the invention, the cranial perforator does not comprise any threaded zone. This prevents any error, especially a wrong screwing during the assembling of the parts of the cranial perforator.

The invention also relates to a kit comprising the set of parts of the cranial perforator according to the invention.

The invention also relates to a method for mounting a kit comprising the set of parts of the cranial perforator according to the invention.

Figure 1:
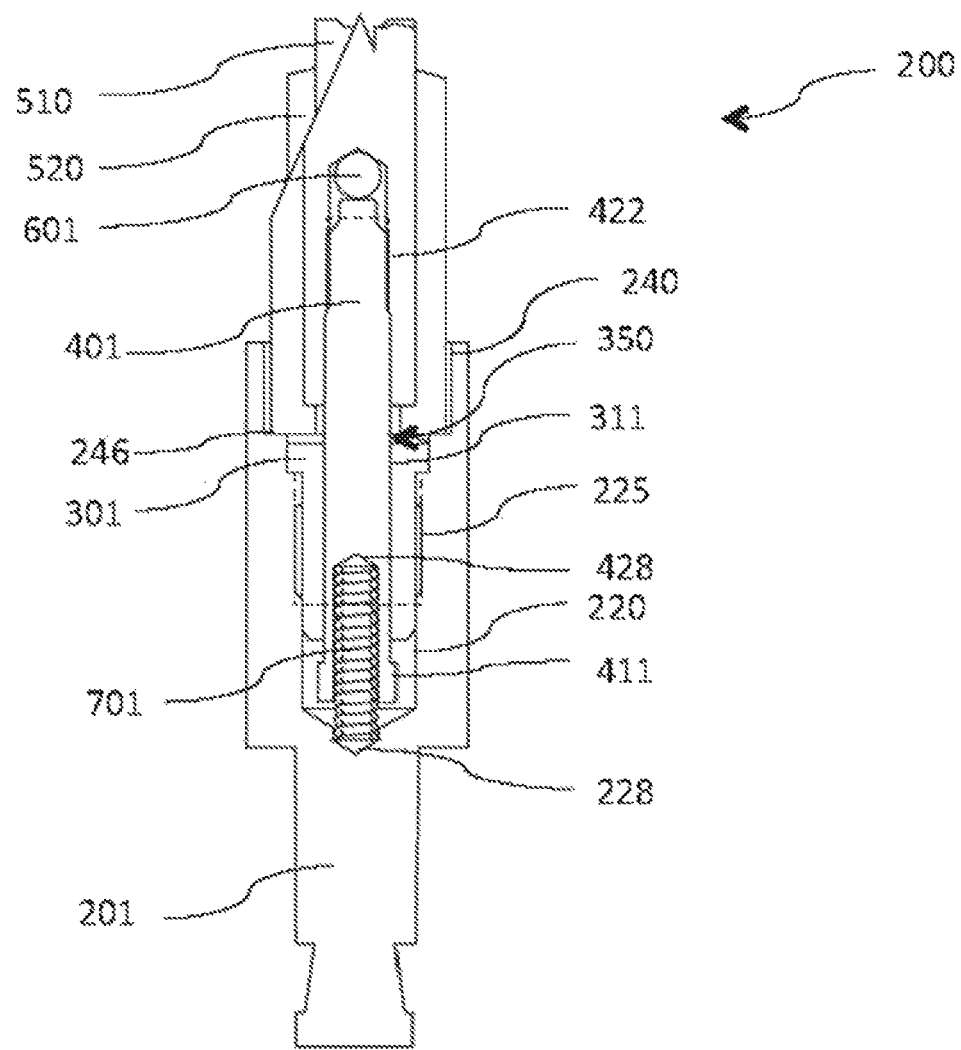
FIG. 1 represents a prior-art cranial perforator as described in the French patent application filed by the present Applicant and published under number FR 2919991.
Figure 2:
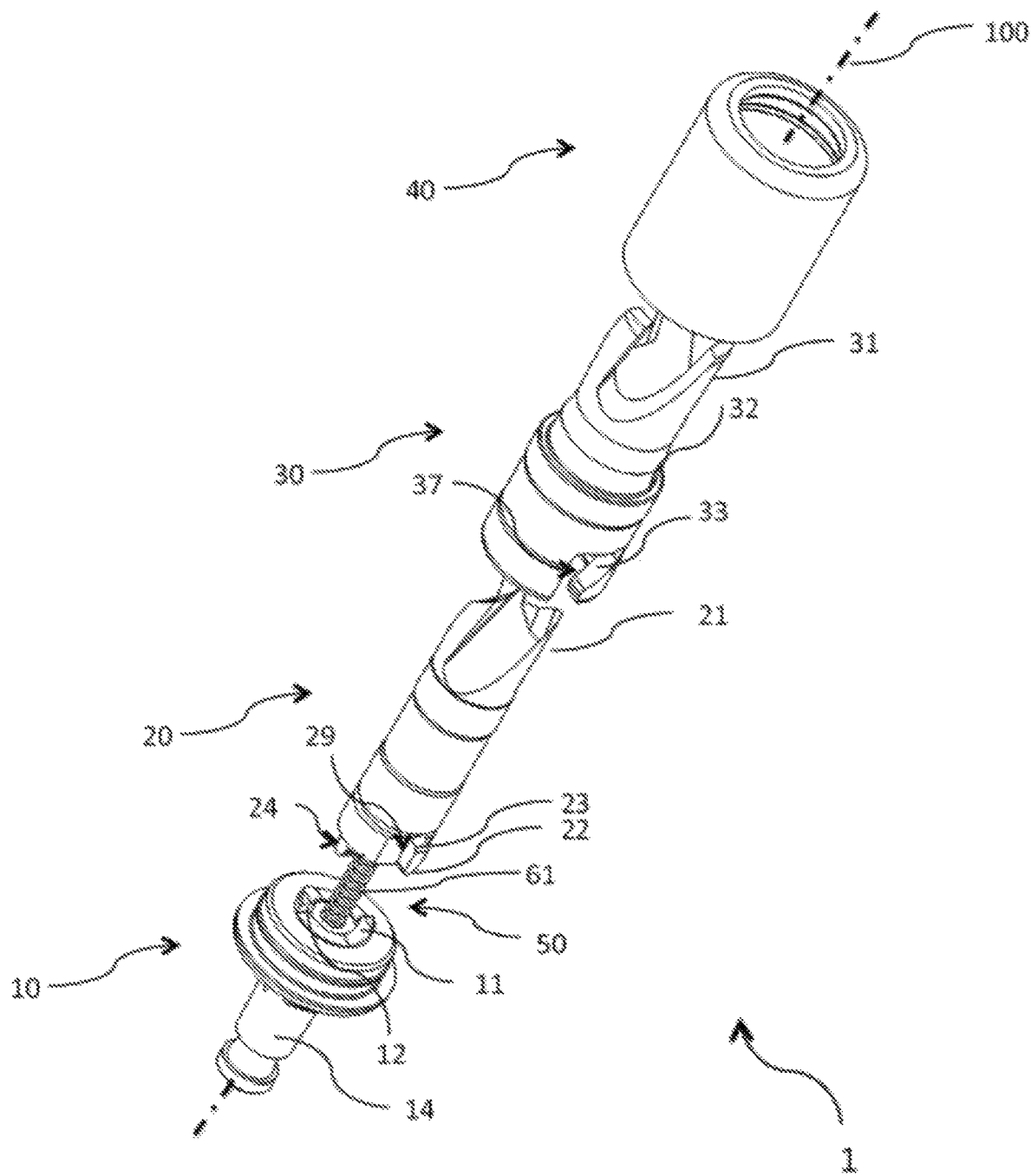

The invention, as well as its different advantages as represented shall be understood more easily from the following description of a non-exhaustive embodiment of this invention given with reference to the appended drawings presented in FIGS. 2-9, wherein:

FIG. 2 represents an exploded three-quarter view of a cranial perforator according to the invention.

FIG. 3A represents a front view of the cranial perforator of FIG. 2. FIG. 3B is a view in section of FIG. 3A passing through the rotation axis of the device.

FIG. 4 and FIG. 5 represent the rotating element of the cranial perforator according to FIG. 2. FIG. 4 is a front view, FIG. 5 is a top view.

FIGS. 6 and 7 represent the first drill-head of the cranial perforator according to FIG. 2. FIG. 6 is a front view. FIG. 7 is a side view.

FIG. 8 represents the second drill-head, seen in a front view, of the cranial perforator according to FIG. 2.

Figure 9:
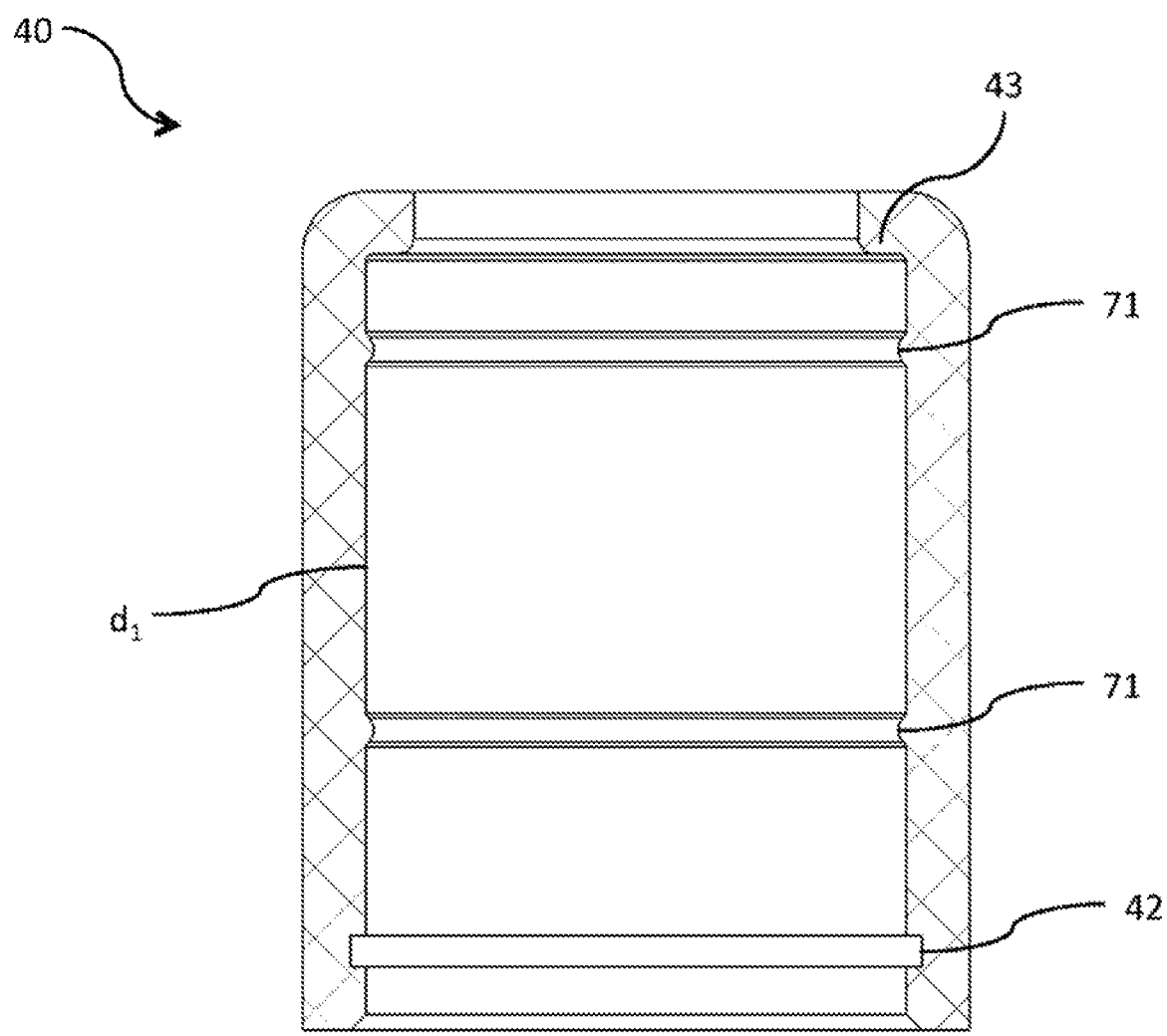

FIG. 9 represents the casing of the cranial perforator according to FIG. 2.

In FIGS. 2-9, the cranial perforator and/or the parts that constitute it are oriented in such a way that the rotating element is below and the teeth of the first drill-head and the second drill-head are above. In the description here below, "above", "upper part", "below", and "lower part" refer to this convention. The axis of the drill-heads according to this convention is therefore a vertical axis in the plane of the drawings.

DETAILED DESCRIPTION

Structure of the Cranial Perforator

Referring to FIGS. 2, 3A and 3B, the cranial perforator 1 comprises five parts: a rotating element 10, a compression spring 61, a first drill-head 20, a second drill-head 30 and a casing 40.

Referring especially to FIGS. 4 and 5, the rotating element 10 comprises at its lower extremity a HUDSON type connection 14, enabling it to be connected to a surgical motor (not shown) implemented in order to put this rotating element 10 into rotation. It can be noted that such a surgical motor (not shown) can put the rotating element 10 into rotation by means of electrical power coming from the mains or stored in batteries, or by means of pneumatic energy.

The rotating element 10 comprises a circular platform 16, surmounted by an essentially cylindrical plate 17. The platform 16 has a diameter larger than that of the plate 17. The platform 16 forms a stop with the casing 40 when this casing is mounted. The plate 17 comprises a circular tongue 18 protruding from the surface of the cylinder.

The plate 17 is surmounted at its central part by two inclined planes 11 interposed between two concentric circles having a diameter smaller than that of the plate 17. Each inclined plane 11 leads on to the upper surface of the plate 17 and is extended by a blocking surface 12 which extends essentially to the vertical, corresponding to the beginning of the other inclined plane 11.

Referring to FIG. 9, the casing 40 essentially has the shape of a hollow cylinder having a cylindrical section with an internal diameter d1 appreciably equal to that of the plate 17. At its lower part, it comprises on its internal surface a circular groove 42 having a shape complementary to that of the circular tongue 18 of the rotating element 10. During the mounting of the cranial perforator 1, the casing 40 is fixed to the rotating element 10 by means of a press. The circular tongue 18 then gets locked into the circular groove 42. This enables an irreversible elastic interlocking between the casing 40 and the rotating element 10. Through this irreversible elastic interlocking, the cranial perforator 1 cannot be dismantled and therefore cannot be cleaned, decontaminated and/or sterilized with a view to a possible second reutilization. The irreversible elastic interlocking of the casing 40 with the rotating element 10 therefore ensures a single-time use of the cranial perforator 1.

The casing 40, at its median part, comprises two circular lips 71 protruding out of its internal surface. The two circular lips 71 ensure a sliding pivot type link 70 between the casing 40 and the second drill-head 30. The sliding pivot link 70 ensures perfect rotation of the second drill-head 30 about its axis 100 as well as the guidance of the second drill-head 30 in translation along its axis 100.

The casing 40 also comprises, at its upper part, a shoulder 43 of a smaller diameter than the diameter of the rest of the cylindrical section of the casing 40. The shoulder 43 forms a stop with the second drill-head 30 in order to limit, to a certain extent, the amplitude of a movement of translation of the second drill-head 30 along its axis 100.

Referring to FIGS. 6-8, the first drill-head 20 and the second drill-head 30 each have at the upper part three teeth 21, 31 distributed at 120°. The teeth 21, 31 have cutting zones 826, 836 projecting and extending essentially from the periphery towards a hollowed-out central zone. The first drill-head 20 is housed inside the second drill-head 30 in such a way that its cutting zone extends beyond the cutting zone of the second drill-head 30. The upper part of the first drill-head furthermore has a pyramidal centering tip 27. The casing 40 obviously does not cover the cutting zones of the first drill-head 20 and the second drill-head 30.

Different batches of the first drill-heads 20 and second drill-heads 30 can have different cutting zones in order to enable a reliable use on different population groups, for example adults, adolescents and children.

The median part and the lower part of the second drill-head 30 are encased by the casing 40. They essentially have the shape of a hollow cylinder having a cylindrical section with an external diameter d2, with d2<d1. The lips 71 are in contact with the walls of the cylinder having an external diameter d2 and thus form the sliding pivot link 70. The friction zones of the sliding pivot link 70 are therefore herein limited as compared with the prior-art technique described here above. It must be noted that FIG. 8 shows a narrowing in the median section. This narrowing reduces the quantity of material used to manufacture the second drill-head 30 on a non-functional part of this drill-head.

The shoulder 32 marks the boundary between the median part and the upper part of the second drill-head 30. The median part has a greater diameter than the bottom of the upper part. The shoulder 32 of the second drill-head forms a stop with the shoulder 43 of the casing 40 and thus limits, to a certain extent, the amplitude of a motion of translation of the second drill-head 30 along its axis 100.

Two essentially triangular notches 37 are drilled from the lower part of the second drill-head 30 to the median part of the second drill-head 30. Each notch 37 includes a ramp 33 that is inclined relative to the axis 100 and terminates at the bottom of the ramp on a rounded portion 34 as well as a plane surface 38 perpendicular to the axis 100.

The ramp 33 thus forms a sliding link 80 with the first drill-head 20. The ramp 33 thus creates an axial force component facilitating the disengagement of the first drill-head 20 during the transmission of the rotation torque between the first drill-head and the second drill-head 30. The ramp 33 can be inclined by an angle of 15° to 75° relative to the axis 100. Preferably, the ramp 33 can be inclined by an angle of 30° to 60° relative to the axis 100. In particular, an angle equal to 45° relative to the axis 100 is particularly advantageous since this makes it possible to obtain efficient transmission of the rotation torque while at the same time facilitating the disengagement of the second drill-head.

The plane surface 38 perpendicular to the axis 100 forms a stop with the first drill-head 20 in order to limit, to a certain extent, the amplitude of a movement of translation of the first drill-head 20 along its axis 100.

The lower extremity of the second drill-head 30 rests in a stopped or abutted position on the plate 17 of the rotating element 10. The lower extremity can be chamfered in order to limit the friction with the plate 17 when the rotating element 10 but not the second drill-head 30 is put into rotation.

The median part of the first drill-head 30 essentially has the shape of a hollow cylinder having a cylindrical section with an external diameter d3, smaller than the internal diameter of the median and lower sections of the second drill-head 30. It must be noted that, in FIG. 6 and FIG. 7, a narrowing of the median section is represented. This narrowing reduces the quantity of material used to manufacture the first drill-head 20 on a non-functional part of this drill-head.

The lower part of the first drill-head 20 includes two spurs 29 projecting radially from the first drill-head 20 and passing through the two notches 37 of the second drill-head 30. Each spur 29 has a first supporting surface 22 capable of abutting the ramp 33 of the second drill-head 30 when the first drill-head 20 is put into rotation. The first supporting surface 22 is rounded and is capable of coming into contact with the ramp 33 thus forming a sliding link. Each spur 29 also comprises a second supporting surface 23 capable of abutting the second drill-head 30 when the first drill-head is driven by a movement of translation moving it away from the rotating element 10 along the axis 100. The second supporting surface 23 is substantially perpendicular to the axis 100 and is capable of forming a stop with the plane surface 38 of the notch 37.

The two spurs 29, and the two notches 37 respectively are disposed anti-symmetrically on said first drill-head 20 and said second drill-head 30 respectively and are thus capable, in sets of two, of forming two sliding links. This makes it possible to house the first drill-head 20 in a unique way relative to the second drill-head 30 especially in order to ensure efficient relative positioning of the teeth 21 of the first drill-head 20 relative to the teeth 31 of the second drill-head 30.

The lower part of the first drill-head 20 also has two fingers 24 extending axially downwards. The two fingers 24 are capable of sliding along the inclined planes 11 of the rotating element and of being blocked by the blocking surfaces 12. More specifically, each finger 24 comprises a supporting surface 25 that is essentially vertical and rounded at its lower extremity enabling the sliding of the finger 24 along the inclined plane 11 and then the formation of a stop against the blocking surface 12.

The two fingers 24 of the first drill-head 20 and the two inclined planes 11 comprising a blocking surface 12 of the rotating element 10 form, in sets of two, the clutch means 50 for engaging the first drill-head 20 with the rotating element 10. The clutch means 50 make it possible, in an engaged position, for the first drill-head 20 to be linked rotationally with the rotating element 10 when the rotating element 10 is put into rotation and make it possible, in a resting position, for the first drill-head 20 to be not linked rotationally with the rotating element 10 when the rotating element 10 is put into rotation. The clutch means 50 are gradual and thus make it possible to prevent any jerking motions during the engaging process.

The two fingers 24 and the two inclined planes 11 respectively comprising a blocking surface 12 are disposed symmetrically relative to the axis 100 on the first drill-head 20 and the rotating element 10 respectively.

A cavity 26 is made along an axis 100 between the fingers 24 of the first drill-head and a cavity 19 is made between the inclined planes 11 along the axis 100 so that the compression spring 61 can be placed therein. The compression spring 61 and the sliding links 80 between the first drill-head 20 and the second drill-head 30, when the first drill-head is put into rotation, constitute the disengagement means of the cranial perforator 1. They enable the rapid disengagement of the first drill-head 20 when the axial force exerted on it is not sufficient, i.e. they enable a return of the first drill-head to an idle position.

Mounting of the Cranial Perforator

The very structure of the elements of the cranial perforator 1 enable a simple assembly that does not require specific tools other than a press in order to be mounted. The very structure of the parts of the cranial perforator 1 also ensure that no error or lack of precision can result from the assembly, since the parts fit into each other in a simple way and since no part has any thread.

To assemble the cranial perforator, the rotating element 10 and the first drill-head 20 must be brought together, and then the compression spring 61 must be inserted into the cavities 19 and 26 made for this purpose. Then, the second drill-head 30 must be fitted over the first drill-head 20 in making sure that the spurs 29 of the first drill-head 20 are properly engaged in the notches 37 of the second drill-head 30. Then, the casing 40 can be fitted over the second drill-head 30, and an irreversible elastic interlocking of the casing 40 with the rotating element 10 which can be obtained by pressing.

Operation of the Cranial Perforator

In order to carry out a perforation of a skull by means of cranial perforator according the invention, a surgeon applies the first drill-head 20 against the surface of the skull that has to be perforated in exerting a certain degree of pressure.

The surgeon then puts the surgical motor in operation, the perforator being connected to this motor by means of a HUDSON type mandrel so that the rotating element 10 is driven rotationally.

The fingers 24 of the first drill-head slide along the inclined planes 11 of the rotating element 10 from their highest part until the supporting surface 25 of the fingers 24 form a stop with the blocking surfaces 12 of the inclined planes 11. This enables a gradual engagement of the first drill-head 20 with the rotating element 10. The torque of the rotating element 10 is then transmitted to the first drill-head 20.

Once the first drill-head 20 is put into rotation, each first supporting surface 22 of the spurs 29 comes into contact with the ramp 33 of each notch 37 of the second drill-head 30. Torque is transmitted between the first drill-head 20 and the rotating element 10 so long as there is a remaining bone thickness before the centering tip 27 of the first drill-head 20.

When there is no longer any bone thickness in front of the centering tip 27 of the first drill-head 20, there is then no longer any axial force that pushes the first drill-head 20 against the rotating element 10. The reaction forces of the compression spring 61 will then push the first drill-head 20 and make it rise by about 1 mm (first disengaging or release travel). To help the compression spring to make the first drill-head 20 rise further, the sliding links 80, formed by the contact of the first supporting surfaces 22 of the spurs 29 with the ramps 33 of the notches 37, will further the ejection, in this first release travel, of the first drill-head 20. Indeed, since the ramps 33 are inclined relative to the axis 100, they enable firstly the transmission of the torque from the first drill-head 20 to the second drill-head 30 and secondly the creation of an axial force component that gets added to the reaction of the compression spring 61 tending to raise the first drill-head 20 relative to the rotating element 10 for gradual and speedier disengagement of the first drill-head 20.

As soon as the first drill-head 20 is no longer engaged with the rotating element 10, the first drill-head 20 gets immobilized and therefore no longer transmits any torque to the second drill-head 30. The perforation stops even if the surgical motor continues to rotate. The practitioner can withdraw the cranial perforator 1 from the skull.

All that the practitioner will have to do then is to remove the bony capsule that has formed, using a spatula. It can be noted that the second drill-head 30 makes it possible, when the first drill-head 20 passes through the bone mass of the skull, to prevent it from continuing its progress towards the interior of the skull and damaging the dura mater.

The invention claimed is:

1. A cranial perforator comprising:
   a rotating element capable of being fixed to a driving element;
   a first drill-head and a second drill-head capable of rotating about a same axis and of moving in translation along said axis and each having, at one of its extremities, a plurality of teeth,
   said first drill-head being housed within said second drill-head,
   said first drill-head comprising in its lower part at least one spur projecting radially from said first drill-head, said spur having a first supporting surface capable of abutting said second drill-head when said first drill-head is put into rotation about said axis and said spur having at least one second supporting surface which is perpendicular to said axis and which is capable of abutting said second drill-head when said first drill-head is driven by a motion of translation moving away from said rotating element along said axis in order to limit an amplitude of a movement of translation of the first drill-head relative to the second drill-head;
   at least one triangular notch being drilled from a lower part of said second drill-head to a median part of said second drill-head, said notch including at least one ramp that is inclined relative to said axis and terminates at a bottom of said ramp on a rounded portion, as well as a plane surface which is perpendicular to said axis and an opposite side to said plane surface which is open;
   clutch means disposed on said first drill-head and said rotating element making it possible, in an engaged position, for said first drill-head to be linked in rotation with said rotating element when said rotating element is put into rotation and making it possible, in an idle position, for said first drill-head not to be linked in rotation with said rotating element when said rotating element is put into rotation, said clutch means comprising at least one inclined plane and a blocking surface disposed on said rotating element, and at least one finger disposed on said first drill-head, said at least one finger having a supporting surface capable of coming into contact with said blocking surface in said engaged position, said supporting surface having a lower rounded extremity for enabling said lower rounded extremity of said supporting surface of said at least one finger to slide along said at least one inclined plane;
   means of disengagement from said engaged position to said idle position, said means of disengagement comprising a return means tending to bring said first drill-head back into said idle position and said means of disengagement comprising said at least one first supporting surface of said first drill-head and said at least one ramp of said at least one triangular notch drilled from said second drill-head and inclined relative to said axis; and
   a casing fixed at one of its extremities to said rotating element and partly encasing said second drill-head, said casing, comprising at its upper part a shoulder, said second drill-head being linked to said casing by a sliding pivot link and comprising a supporting surface capable of abutting said shoulder of said casing when said second drill-head is driven by a movement of translation moving away from said rotating element along said axis in order to limit the amplitude of said movement of translation.

2. The cranial perforator according to claim 1, characterized in that said casing comprises a cylindrical section with a diameter greater than the diameter of a cylindrical section of the second drill-head, said sliding pivot link being formed by at least one lip protruding out of an external surface of said cylindrical section of said second drill-head or an internal surface of said cylindrical section of said casing.

3. The cranial perforator according to claim 2, characterized in that said sliding pivot link is formed by two lips protruding out of an external surface of said cylindrical section of said second drill-head or out of an internal surface of said cylindrical section of said casing.

4. The cranial perforator according to claim 1, characterized in that said casing is fixed to said rotating element by an irreversible elastic interlocking of said casing with said rotating element.

5. The cranial perforator according to claim 1, characterized in that an angle formed between said at least one ramp and said axis ranges from 15° to 75° relative to said axis.

6. The cranial perforator according to claim 1, characterized in that said first drill-head comprises two spurs of said at least one spur projecting radially from said first drill-head, each of said two spurs having one said first supporting surfaces capable of forming two sliding links with two ramps disposed on said second drill-head and the two ramps and the two first supporting surfaces respectively do not get superimposed by rotation by an angle of 180° along said axis.

7. The cranial perforator according to claim 1, said cranial perforator comprising no threaded zone.

8. The cranial perforator according to claim 1, characterized in that an angle formed between said at least one ramp and said axis ranges from 30° to 60° relative to said axis.

9. The cranial perforator according to claim 1, characterized in that an angle formed between said at least one ramp and said axis is equal to about 45° relative to said axis.

10. The cranial perforator according to claim 1, wherein the return means comprise a compression spring.

* * * * *